(12) United States Patent
Richard

(10) Patent No.: US 7,715,602 B2
(45) Date of Patent: May 11, 2010

(54) METHOD AND APPARATUS FOR RECONSTRUCTING BONE SURFACES DURING SURGERY

(75) Inventor: Alain Richard, MLT (CA)

(73) Assignee: Orthosoft Inc., Montréal (CA)

( * ) Notice: Subject to any disclaimer, the term of this patent is extended or adjusted under 35 U.S.C. 154(b) by 1718 days.

(21) Appl. No.: 10/345,403

(22) Filed: Jan. 16, 2003

(65) Prior Publication Data

US 2003/0225415 A1 Dec. 4, 2003

Related U.S. Application Data

(60) Provisional application No. 60/349,267, filed on Jan. 18, 2002.

(51) Int. Cl.
G06K 9/00 (2006.01)
A61B 5/05 (2006.01)

(52) U.S. Cl. ............... 382/128; 382/131; 382/132; 600/407; 600/424; 600/426; 606/87; 606/88; 606/130

(58) Field of Classification Search .......... 382/128, 382/131, 132; 600/424, 426
See application file for complete search history.

(56) References Cited

U.S. PATENT DOCUMENTS

| | | | | |
|---|---|---|---|---|
| 4,936,862 A | | 6/1990 | Walker et al. | |
| 5,564,437 A | * | 10/1996 | Bainville et al. | 600/587 |
| 5,622,170 A | * | 4/1997 | Schulz | 600/424 |
| 5,649,929 A | | 7/1997 | Callaway | |
| 5,682,886 A | * | 11/1997 | Delp et al. | 600/407 |
| 5,688,280 A | | 11/1997 | Booth, Jr. et al. | |
| 5,748,767 A | * | 5/1998 | Raab | 382/128 |
| 5,765,561 A | * | 6/1998 | Chen et al. | 600/407 |
| 5,772,594 A | | 6/1998 | Barrick | |
| 5,806,518 A | * | 9/1998 | Mittelstadt | 600/407 |
| 5,823,778 A | | 10/1998 | Schmitt et al. | |
| 5,824,083 A | | 10/1998 | Draenert | |
| 5,871,018 A | | 2/1999 | Delp et al. | |
| 6,006,126 A | * | 12/1999 | Cosman | 600/426 |
| 6,023,495 A | * | 2/2000 | Adler et al. | 378/4 |
| 6,033,415 A | * | 3/2000 | Mittelstadt et al. | 606/130 |
| 6,051,028 A | | 4/2000 | McCartney et al. | |

(Continued)

FOREIGN PATENT DOCUMENTS

EP 0919203 6/1999

(Continued)

OTHER PUBLICATIONS

Radiological Analysis of Normal Axial Alignment of Femur and Tibia in View of Total Knee Arthroplasty, The Journal of Arthroplasty, vol. 8 N° 4, 1993 -by Michael H. Oswald et al., pp. 419-426.

(Continued)

*Primary Examiner*—Aaron W Carter
*Assistant Examiner*—Gandhi Thirugnanam
(74) *Attorney, Agent, or Firm*—Ogilvy Renault LLP

(57) ABSTRACT

There is provided a method for intra-operatively presenting an approximate model of an anatomical structure by collecting a cloud of small surfaces. The cloud of small surfaces is gathered with a registration pointer having an adapted tip capable of making contact with the surface of an anatomical structure and registering the normal at the point of contact.

31 Claims, 5 Drawing Sheets

U.S. PATENT DOCUMENTS

| | | | |
|---|---|---|---|
| 6,056,756 A | | 5/2000 | Eng et al. |
| 6,161,080 A * | | 12/2000 | Aouni-Ateshian et al. .... 703/11 |
| 6,177,034 B1 | | 1/2001 | Ferrone |
| 6,285,902 B1 * | | 9/2001 | Kienzle et al. .............. 600/427 |
| 6,322,567 B1 | | 11/2001 | Mittelstadt et al. |
| 2002/0120192 A1* | | 8/2002 | Nolte et al. .................. 600/424 |
| 2003/0176783 A1* | | 9/2003 | Hu .............................. 600/429 |
| 2005/0015022 A1* | | 1/2005 | Richard et al. ............... 600/587 |
| 2005/0148860 A1* | | 7/2005 | Liew et al. ................... 600/410 |
| 2005/0182319 A1* | | 8/2005 | Glossop ....................... 600/424 |
| 2005/0228266 A1* | | 10/2005 | McCombs ................... 600/414 |
| 2005/0288574 A1* | | 12/2005 | Thornton et al. ............ 600/423 |
| 2006/0089609 A1* | | 4/2006 | Bleich et al. ................. 604/272 |
| 2006/0135882 A1* | | 6/2006 | Bleich ......................... 600/546 |
| 2006/0258951 A1* | | 11/2006 | Bleich et al. ................. 600/546 |
| 2008/0262345 A1* | | 10/2008 | Fichtinger et al. ........... 600/426 |

FOREIGN PATENT DOCUMENTS

| | | |
|---|---|---|
| EP | 1 226 788 A1 | 7/2002 |
| WO | WO95/00075 | 1/1995 |
| WO | WO98/40037 | 9/1998 |
| WO | WO99/59106 | 11/1999 |
| WO | WO99/60939 | 12/1999 |
| WO | WO/0054687 | 9/2000 |
| WO | WO 01/35842 | 5/2001 |
| WO | WO01/67979 | 9/2001 |
| WO | WO02/36031 | 5/2002 |

OTHER PUBLICATIONS

Mise en Place des Prothéses totales du genou assistée par ordinateur: Comparaison avec la technique conventionnelle, Revue de Chirurgie orthopédique 2001, 87 by Aeculap A.G. Tuttlingen, Allemagne, Sep. 11, 2000, pp. 18-28.

Radiographic Analysis of the Axial Alignment of the Lower Extremity, vol. 69-A, N° 5, Jun. 1987, by John R. Moreland et al., pp. 745-749.

An Anatomy-Based Coordinate System for the Description of the Kinematic Displacements in the Human Knee, J. Biomechanics, vol. 23, No. 12, 1990, by G.R. Pennock et al., pp. 1209-1218.

The Anatomy and Functional Axes of the Femur, Journal of Bone and Join Surgery, Inc., vol. 69-A, N° 6, Jul. 1987, by Yuki Yoshioka et al, pp. 873-880.

Tibial Anatomy and Functional Axes, Journal of Orthopaedic Research, 1989 by Yuki Yoshioka et al., pp. 132-137.

Determining the Rotational Alignment of the Femoral Component in Total Knee Arthroplasty Using the Epicondylar Axis, by Richard A. Berger et al, presented by the Seventh Open Scientific Meeting of the Knee Society, Washington, DC., Feb. 23, 1992, pp. 40-47.

Assessment of Center of Rotation of the Glenohumeral Joint, by Marjolein van der Glas et al., Niessen and M. Viergever, MICCAI 2001, LNCS, pp. 1207-1209.

Abstract—On the Estimation of Joint Kinematics During Gait, by HK Ramakrishnan et al., J. Biomech 1991: 24(10):969-77.

Abstract—Kinematic Analysis of Lower-Limb Movement during Ergometer Pedaling in Hemiplegic and Nonhemiplegic Subjects, Phys. Ther 1991, Apr. 1971 (4): 334-43 by J. C. Rosecrance et al.

Abstract—A three-dimensional Kinematic and Dynamic Model of the Lower Limb, J. Biomech 1989; 22(2) by J. Apkarian et al. pp. 143-155.

Abstract—Optimal Marker Placement for Calculating the Instantaneous Center of Rotation, J. Biomech Sep. 27, 1994 (9) : 1183-7 1183-1187 by JJ Crisco $3^{rd}$, et al.

Abstract—A New Method for Estimating the Axis of Rotation and the Center of Rotation, J. Biomech Nov. 1999, 32(11):1221-1227, by K. Halvosen et al.

Abstract—Determination of Femoral Head Containment during Gait, Biomater Med Devices Artif Organs, 1981, 11 (1) : 31-38 by G.T. Rab.

Abstract —A Technique for Determining Femoral Head Containment During Gait, J. Pediatr Orthop 1981, Jan.-Feb., 5(1) : 8-12 by G.T. Rab et al.

Abstract—Movement Loci of Selected Points on the Femoral Head for Individual Total Hip Arthroplasty Patients Using Three-Dimensional Computer Simulation, J Arthroplasty Oct. 2000, 15(7): 909-15, by D.B. Bennett et al.

Three-Dimensional Finite Element Analy6sis of Legg-Calve-Perthes Disease, J Pediatr Orthop Mar. 1981, 2(1) : 39-44 by G.T. Rab et al.

Abstract—A Relationship Between Stem Orientation and Function Following Total Hip Arthroplasty, J. Arthroplasty Sep. 1991, 6(3) : 229-235. by W.A. Hodge et al.

Abstract—Slipped Capital Femoral Epiphysis. A Quantitative Analysis of Motion, Gait, and Femoral Remodeling After in situ Fixation, J. Bone Joint Surg. Am. Jun. 1991; 73(5) : 659-66 by D.B. Siegel et al.

Fixed- Versus Mobile-Bearing Total Knee Arthroplasty: Technocal Issues and Surgical Tips, by Lawrence S. Crossett, MD. Feb. 2002, www.orthobluejournal.com Apr. 16, 2003, pp. 1-10.

* cited by examiner

METHOD AND APPARATUS FOR RECONSTRUCTING BONE SURFACES DURING SURGERY

CROSS REFERENCE TO RELATED APPLICATIONS

This application claims priority of provisional application of the same title filed Jan. 18, 2002, Ser. No. 60/349,267 and of PCT application of the same title filed Jan. 16, 2002, serial number PCT/CA02/00047 now withdrawn.

FIELD OF THE INVENTION

The invention relates to the field of computer-assisted surgery or image-guided surgery. More specifically, it relates to the reconstruction of the surface of a bone during surgery.

BACKGROUND OF THE INVENTION

As technology allows us to advance in the field of computer-aided surgery, such systems are becoming more specialized and refined. The advances made for orthopedic surgery are particularly impressive. These systems allow surgeons to prepare for surgery by viewing 3D models of patients' anatomy that were reconstructed using pre-operative images such as scans and x-rays. Virtual planning markers can be inserted into three-dimensional images at any sites of interest and the ideal implant or prosthesis can be designed for a specific patient by constructing virtual implant models and simulating the results with the reconstructed model.

Furthermore, during surgery, many surgical instruments are now tracked and can be displayed on the reconstructed 3D models to provide surgeons with a reference as to where they are within a patient's body. This is a precious asset in surgeries that involve delicate procedures that allow the surgeon very little room to maneuver. Unfortunately, this feature can only be taken advantage of when a 3D reconstruction of the patient's structure has been made. This is done pre-operatively using various imaging technologies and can become quite time-consuming for a surgeon.

However, it is desirable to cut down the pre-operative time a surgeon must spend to prepare a surgery. It is also desirable to develop an application that can use other media than Computer-Tomographic (CT) scans, when these are not available.

Moreover, since it is advantageous to provide a surgeon with visual confirmation of the tasks he is performing during the surgery, there is a need to develop a CT-less intra-operative bone reconstruction system.

SUMMARY OF THE INVENTION

Accordingly, an object of the present invention is to reduce pre-operative time in surgical procedures.

Another object of the present invention is to reduce the time of instrumentation calibration in surgical procedures.

A further object of the present invention is to provide a simple CT-less system to use for simple surgical cases that can be used in combination with a CT-based system for difficult surgical cases.

According to a first broad aspect of the present invention, there is provided a method for intra-operatively presenting an approximate model of an anatomical structure, the method comprising: applying a registration tool having a position sensing system associated therewith to a plurality of locations on the anatomical structure; acquiring input data using the registration tool such that a point is registered for each of the locations; processing the input data into an approximate model of the anatomical structure; and displaying the approximate model on an output device, Preferably, the registration too(is provided with a tip adapted for making contact with the surface of an anatomical structure and registering the normal at the point of contact. Also preferably, a cloud of points is displayed as a mosaic on the output device. Alternatively, the cloud of points is smoothed over and a smoothed surface is displayed on the output device. The points at which the data was acquired may also be displayed on the smoothed surface. Also alternatively, a three dimensional reconstruction is done based on the acquired input data.

Additionally, a database of known models of the anatomical surface may be used to attach to the portion of the anatomical surface represented by the cloud of points, the smoothed surface, or the three dimensional reconstruction.

According to a second broad aspect of the present invention, there is provided a system for displaying an approximate model of a surface of an anatomical structure, the system comprising: a registration tool having a first end adapted for applying to a surface of an anatomical structure; a position sensing system associated to the registration tool for acquiring input data representing a plurality of locations on the surface of an anatomical structure such that a position and orientation of the registration tool is determined at each of the plurality of locations; a storing module for receiving and storing said input data from the position sensing system; a processing module for processing the input data into an approximate model of the anatomical structure; and an output device for displaying the approximate model of the anatomical structure.

Preferably, the processing module may also perform either a smoothing of a surface or a reconstruction of a three dimensional model. Also, a database of known models may be present to attach to any portion of the anatomical surface represented by the acquired input data in order to display an entire model of the anatomical surface.

Also preferably, the registration tool has a tip adapted for making contact with the surface of an anatomical structure and registering the normal at the point of contact. The normal for each point of contact is comprised in the input data and used in the representation of the anatomical surface.

According to a third broad aspect of the present invention, there is provided a registration tool for intra-operatively acquiring data representing an approximate model of an anatomical structure, the tool having an adapted tip at a first end such that an anatomical surface and a normal to the anatomical surface are registered when the tip is applied to the anatomical structure.

Preferably, the tool is a double ended tool with a first flat surface at the first end and a second flat surface at a second end also adapted to determine the normal at a point of contact. The first flat surface and the second flat surface have different dimensions. Alternatively, the second end may comprise another intra-operative tool.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

For the purpose of this description, a total knee replacement surgery will be used to demonstrate the invention. However, it can be appreciated that the invention can be used to reconstruct the surface of any anatomical structure in a body.

Figure 1:
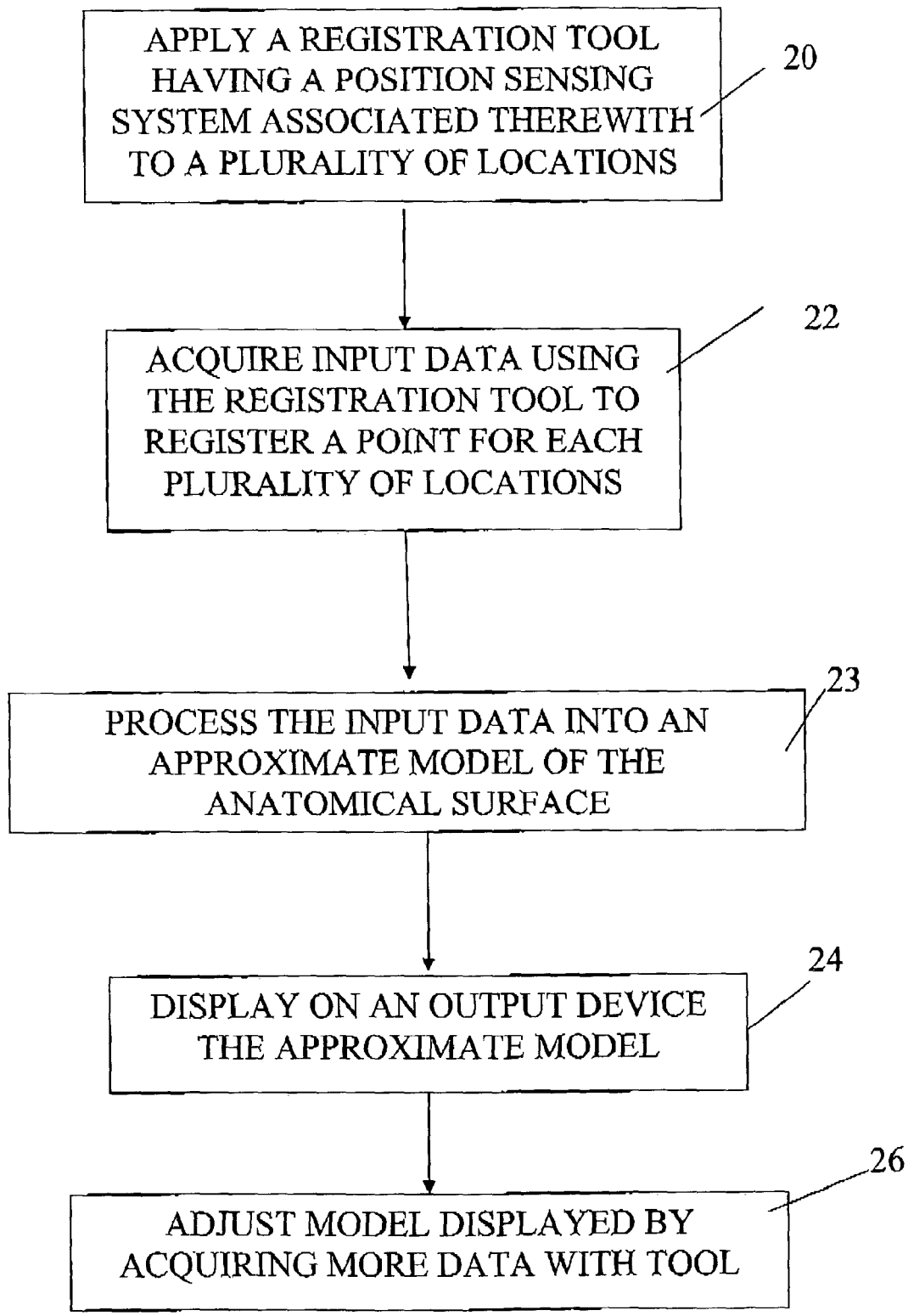
FIG. 1 is a flowchart of the method in accordance with the invention.

FIG. 1 is a flowchart describing the steps used to intra-operatively present an approximate model of an anatomical structure on an output device. The first step is to apply a registration tool to the anatomical surface 20. This tool can be a standard digitizing pointer, a laser pointer, or any other registration tool known to a person skilled in the art. A position sensing system must be associated to the tool to track the position and orientation of the registration tool as it moves over the surface of the anatomical structure. In a preferred embodiment, an infrared, light reflecting tracking system having at least three reflectors is used. Alternatively, any mechanical, electromagnetic, or optical position sensing system may be used. The next step consists in acquiring input data at each point of contact 22.

Figure 2:
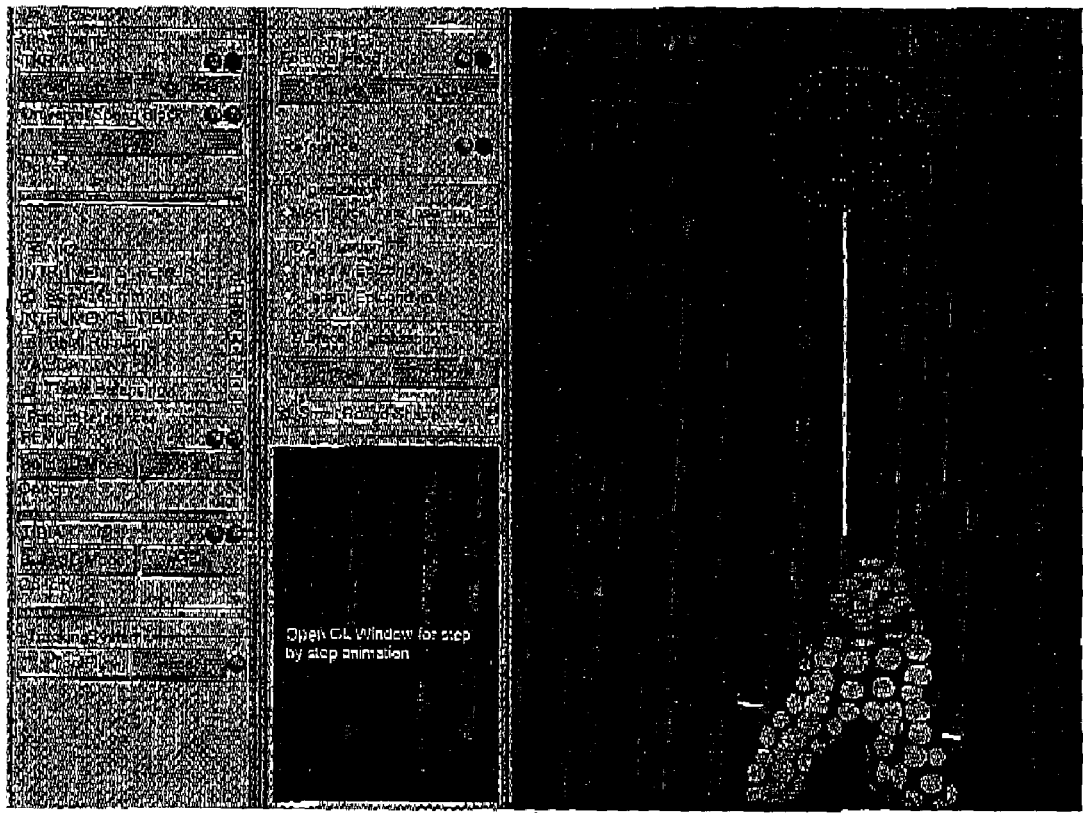
FIG. 2 shows the mosaic reconstruction of a bone.
Figure 3:
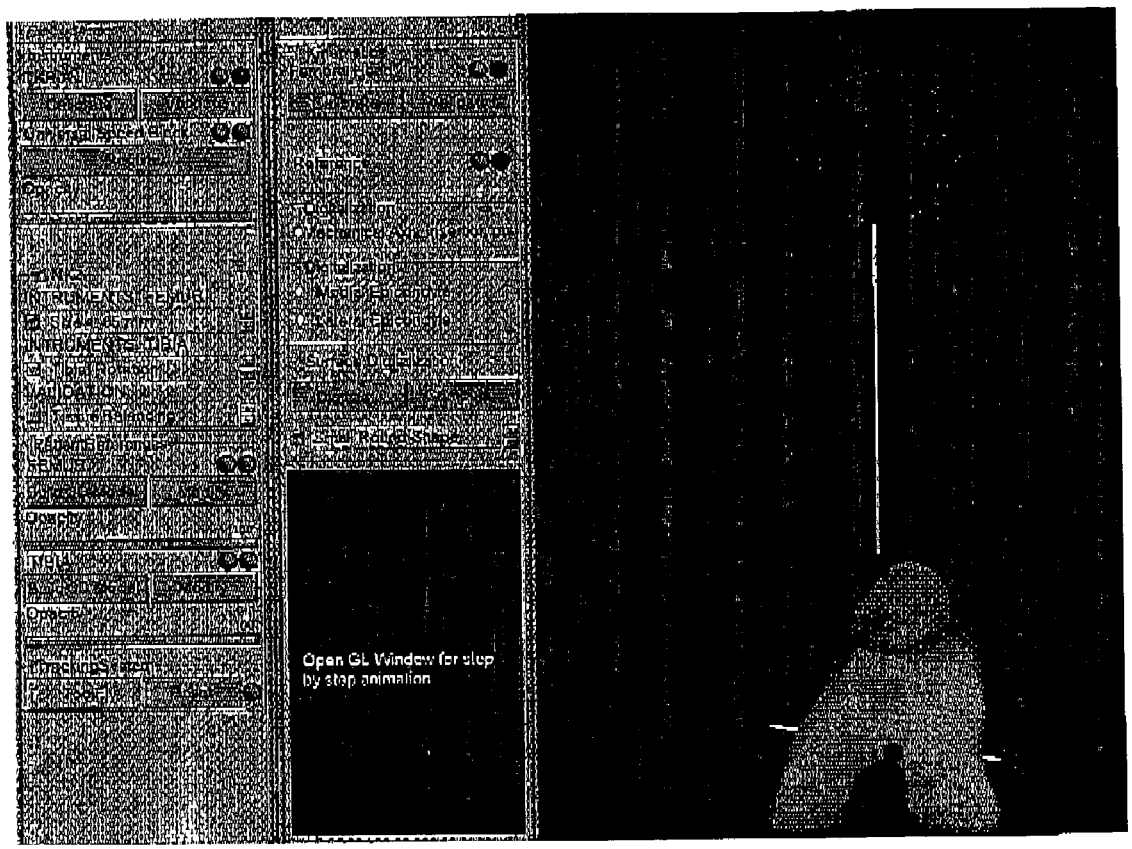
FIG. 3 shows the reconstructed bone after smoothing.

In a preferred embodiment, the normal at each point of contact is determined and included in the input data. A tool having a small flat surface, such as a small disc, is used to acquire the data such that instead of registering only a point, a small surface is registered at each point of contact. The input data is then processed into an approximate model of the anatomical surface 23 and is then displayed on the output device 24, The processing may simply comprise transforming the input data into a cloud of points forming a mosaic representing a portion of the anatomical structure that was digitized. An example of a portion of a femur bone is shown represented by a cloud of points in FIG. 2. Alternatively, the input data may be smoothed over to be displayed as a smoothed surface representing a more accurate surface topology of the portion of the anatomical structure that was digitized. An example of the same femur bone portion smoothed over can be seen in FIG. 3. It can be seen from this figure that the normal of each point of contact was taken into consideration when the points were registered A surface topology is evident from the displayed surface.

The input data may also be used to reconstruct a three dimensional model of the portion of the anatomical structure that was digitized. This requires a more complex processing of the input data than a simple smoothing over. Alternatively, the points registered may be matched to a known model of the same anatomical structure and the model is displayed on the output device with the digitized points indicated on the model. This way, the entire bone can be visualized during the surgery. Alternatively, the input data may be used to reconstruct an entire model of the anatomical surface using extrapolation of the input data.

Another way to display an entire anatomical structure is to attach a portion of a known model to the portion digitized using the registration tool. For example, if the portion of a femur that is digitized consists of the anterior cortex, the condylar surface, and the inter-condylar notch, then a shaft portion and a femoral head from a known model having similar dimensions can be attached to the digitized portion and displayed as an entire femur. The known model can be attached to a cloud of points forming a mosaic, a smoothed surface, or a three dimensional reconstruction.

Optionally, the model of the anatomical structure displayed on the output device may be adjusted by acquiring more points to better represent the actual topology of the anatomical structure. As more data is acquired, the model displayed is updated to reflect the new information.

Once a model representing the anatomy is displayed on the output device, tools used for the surgery can be tracked with respect to this model, thereby allowing the surgeon to navigate with tools and have a reference in the body.

The surface model reconstruction is a process that allows the user to digitize small surfaces instead of points only. These surfaces can be small circles, as can be seen from FIG. 2. The small circle is physically present on the tip of the registration tool as a small, flat disc. The size of the disc (radius) is chosen as a compromise between accuracy and time. It is counter-productive to ask a surgeon to take hundreds of points when digitizing the surface of a bone. However, the more points taken, the better the representation of the bone and the more accurate the model. The size can also vary depending on the morphology of the bone surface, affecting the precision of the tool. For example, the disc could cover an area of 1 $cm^2$. The disc must be flat on the surface to register as much surface as possible. The tool also registers the normal at the point of contact between the flat disc surface and the bone. The reconstruction is done in real time.

Figure 4:
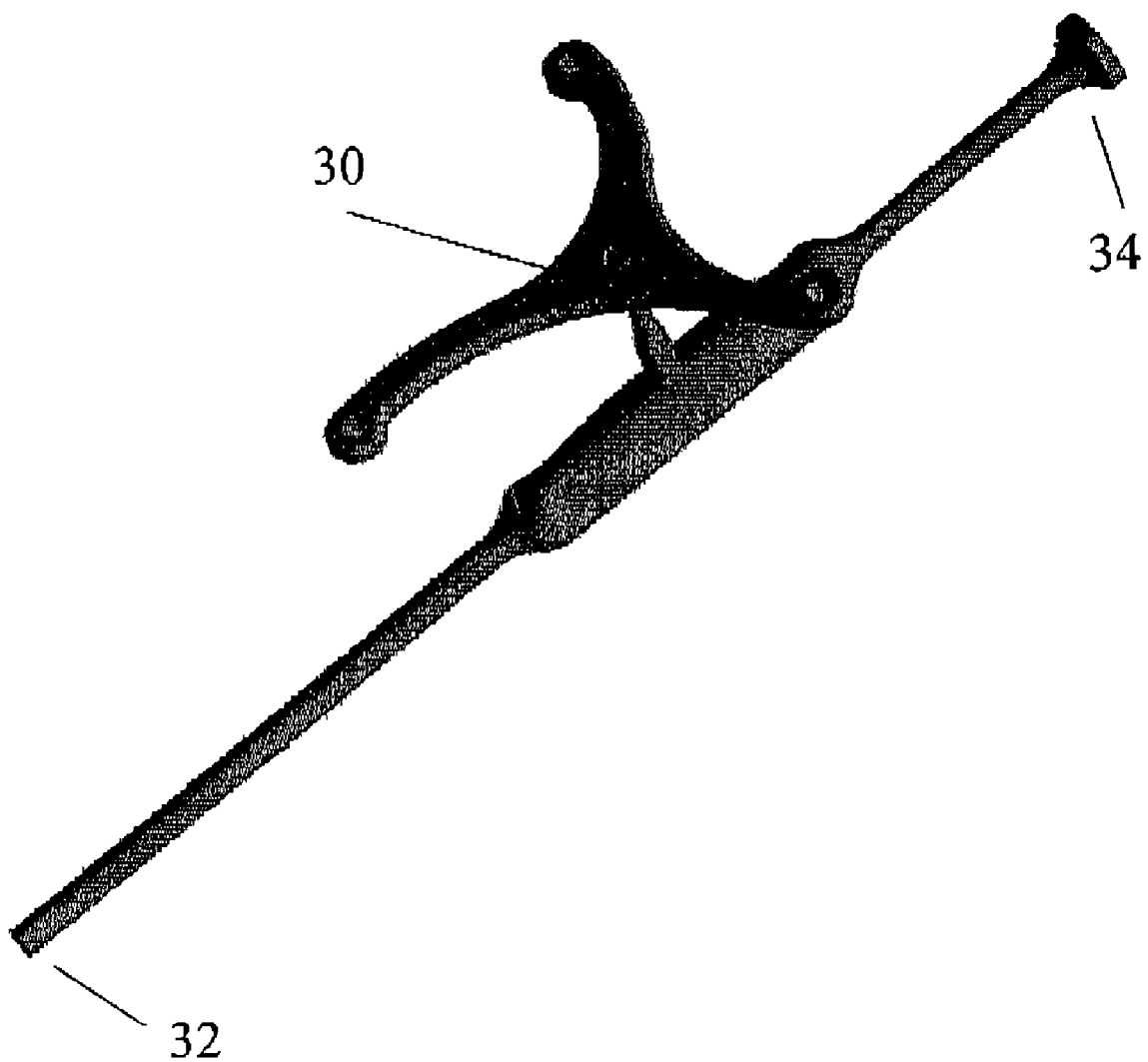
FIG. 4 is a diagram of a registration tool with an adaptive tip.

FIG. 4 is the preferred embodiment of the registration tool to be used in the digitizing process. The tool is equipped with a position-sensing device 30, such as those known in the field of tracking, having three position identifying devices. In this embodiment, both ends of the tool can serve as a digitizing tip, each end having a different radius. The smaller end 32 can be used on anatomical surfaces that do not easily accommodate the flat surface of the tool. The larger end 34 can be used on flatter anatomical surfaces. The user selects on the computer which end is used. Alternatively, there can be automatic detection of the end being used, such as the computer recognizing the radius of the disc surface when it is placed on the bone surface. For the actual registration of the small surfaces, this can be achieved in several ways. For example, there can be a button on the tool that controls the digitizing. Alternatively, this can be done by pressing a key on a keyboard to select a point to be digitized. Also alternatively, digitizing can be triggered by a rotating action of the tool by a quarter turn. It can be appreciated that alternative embodiments for the registration tool are possible. For example, other multi-purpose combinations can be made. One end can be an awl, a screwdriver, or a probe, while the other end is a digitizer. Similarly, the tool can be a single-ended digitizer as well.

Figure 5:
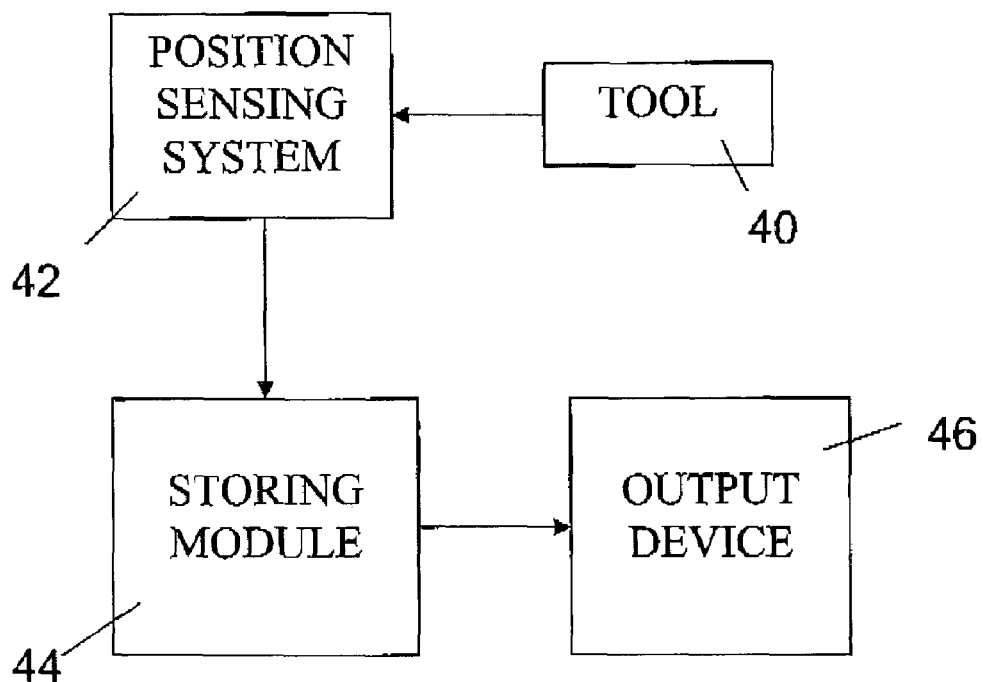
FIG. 5 is a block diagram of the system in accordance with the invention.

FIG. 5 shows the system for displaying an approximate model of a surface of an anatomical structure in accordance with the present invention. A registration tool 40 sends data to a position sensing system 42 corresponding to its position and orientation relative to an anatomical structure. The tool 40 is tracked by the position sensing system 42 in a three-dimensional environment. The orientation and position of the tool 40 is captured by the position sensing system and transferred to a storing module 44. The data is then sent to an output device 46, such as a monitor, to display to the user.

Figure 6:
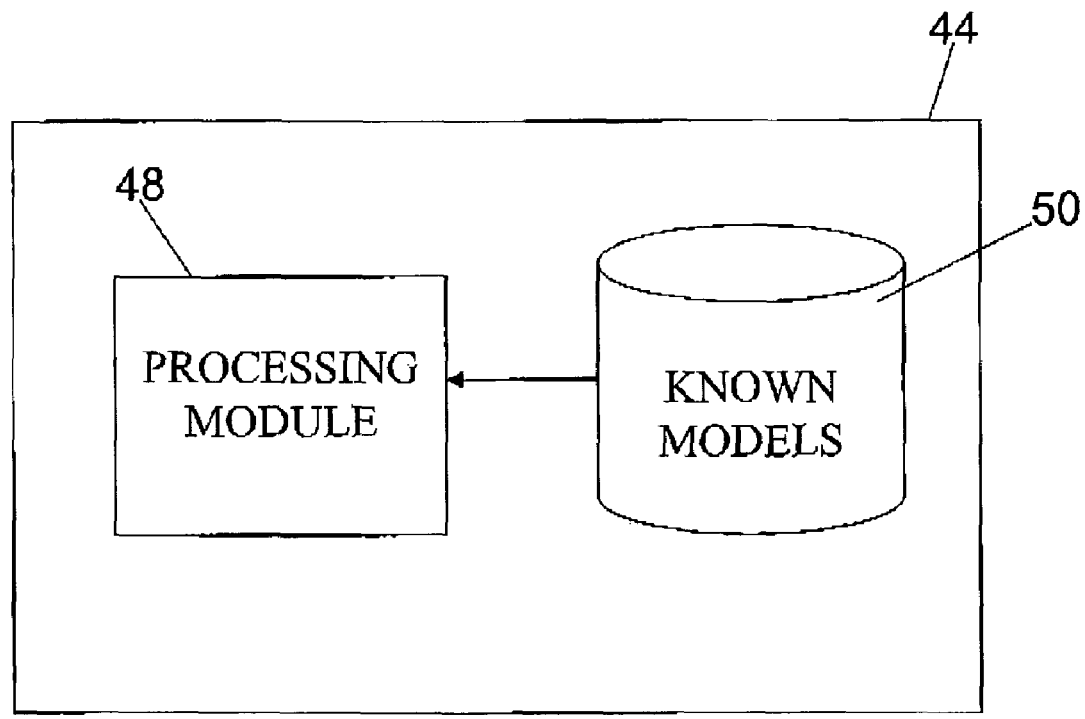
FIG. 6 is a block diagram of a portion of the system of FIG. 5.

FIG. 6 is a block diagram of the storing module 44 in a preferred embodiment. When the data indicating the position and orientation of the tool 40 is received by the storing module 44, it may be processed in various ways. A processing module 48 is used to smooth over the mosaic surface formed by the data recorded by the tool 40 The initial bone registration procedure is done by collecting information on the surface of the bone. The information collected is the position and orientation of the bone surface at each point of contact. The normal of the digitized surface is calculated using the mean value of the orientation of the registration tool 40, which is collected by the sensing system 42. The processing module 48 receives the orientation and position information and uses a surface-modeling algorithm, such as the marching cubes algorithm, to provide a smoothed over surface of the bone topology. It can be appreciated that any surface-modeling algorithm known in the art can be used to perform the smoothing procedure. Optionally, the points at which the initial data was gathered may also be displayed on top of the smoothed surface.

Alternatively, the processing module 48 may perform a three-dimensional reconstruction of a bone using the position and orientation data gathered by the registration tool 40. This reconstruction is similar to a three dimensional reconstruction of a bone done pre-operatively using other types of data gathering devices such as CT-scans and other scanning devices. In one embodiment, the three dimensional reconstruction is done independently of any standard or known shape and size of bone. In a varying embodiment, a database of known models 50 is available to the processing module 48. In this case, the reconstruction is based on known models. The registered points are matched using a best-fit algorithm to a known model of similar size and shape as the anatomical structure under examination. The reconstructed shape is then displayed on the output device 46. The matched points may be displayed on top of the three dimensional shape. In another embodiment, the known models are simply used as a reference for the three dimensional reconstruction. The reconstruction algorithm simply uses the known models as a guide in reconstructing a full three dimensional model, The known models database 50 comprises a plurality of anatomical structures of varying sizes and shapes. The processing module 48 accesses the database 50 and selects a model of similar size and shape to the anatomical structure undergoing operation. The database 50 may also comprise portions or parts of complete anatomical structures. For example, in the case of a femur bone, the database may comprise femoral heads of different sizes and shapes, or femoral shafts of different sizes and shapes. These parts of anatomical structures are used to attached any one of three dimensional reconstructions, smoothed over surfaces, or clouds of points forming a portion of an anatomical structure. The attached portion provides a more complete visual tool to the surgeon during the surgical procedure. Intra-operative time is saved by limiting the amount of digitizing necessary to have a faithful representation of the areas of interest on the anatomical structure. A better visual tool is provided for guidance during surgical navigation with a computer assisted surgical navigation system.

The above described system may be used independently, or with a complete computer assisted surgical navigation system. Once the intra-operative registration is complete and a representation of the anatomical structure is displayed on the output device, a plurality of surgical tools may be tracked and displayed with respect to the intra-operative representation. Cutting guides and positioning blocks may be tracked and used in conjunction with the displayed representation.

The method and system described above may be used on cadavers or dummies in order to test a computer aided surgery system. Testing of new equipment such as a new tracking system, a positioning block, a cutting guide, or so on can also be done in conjunction with the method and system of the present invention. The method and system described may also be used on cadavers or dummies as a teaching tool for medical students. Real life situations may be simulated using the system in order to practice various surgical procedures without the risks posed to a patient.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for intra-operatively presenting an approximate model of an anatomical structure, the anatomical structure being a bone, the method comprising:
    applying a registration tool having a position sensing system associated therewith directly in contact against a plurality of locations on said bone;
    acquiring input data using said registration tool such that the input data consists of at least a point registered for each of said locations;
    processing said input data into an approximate model of said bone without using an image of the anatomical structure taken pre-operatively or intra-operatively; and
    displaying said approximate model without any image of the anatomical structure taken pre-operatively or intra-operatively, and with a surgical tool having the position sensing system associated therewith on an output device during a navigation in surgery.

2. A method as claimed in claim 1, wherein said processing comprises processing said input data into a cloud of points forming a mosaic and representing a portion of said anatomical structure.

3. A method as claimed in claim 1, wherein said processing comprises smoothing over a surface represented by said input data to display a smoothed surface of a portion of said anatomical structure.

4. A method as claimed in claim 3, wherein said processing comprises providing on said smoothed surface said plurality of locations where said input data was acquired.

5. A method as claimed in claim 4, comprising repeating said acquiring input data after said displaying to adjust said model of said anatomical structure.

6. A method as claimed in claim 1, wherein said processing comprises reconstructing a three dimensional model using said input data to display a three dimensional model of a portion of said anatomical structure.

7. A method as claimed in claim 1, wherein said processing comprises reconstructing a three dimensional model using said input data and a known model of said anatomical structure to display a three dimensional model of said anatomical structure.

8. A method as claimed in claim 1, wherein said processing comprises selecting a known model from a known model database comprising a plurality of known models of varying sizes and shapes and performing an algorithm to determine a best-fit match of said input data onto said known model.

9. A method as claimed in claim 8, wherein said processing comprises providing on said known model said best-fit match such that said best-fit match is displayed on said output device.

10. A method as claimed in claim 2, wherein said processing comprises attaching a portion of a known model of said anatomical structure to said mosaic representing a portion of said anatomical structure, said known model representing a remaining portion of said anatomical structure such that an entire model of said anatomical structure is displayed.

11. A method as claimed in claim 3, wherein said processing comprises attaching a portion of a known model of said anatomical structure to said smoothed surface of a portion of said anatomical structure, said known model representing a remaining portion of said anatomical structure such that an entire model of said anatomical structure is displayed.

12. A method as claimed in claim 6, wherein said processing comprises attaching a portion of a known model of said anatomical structure to said three dimensional model of a portion of said anatomical structure, said known model representing a remaining portion of said anatomical structure such that an entire model of said anatomical structure is displayed.

13. A method as claimed in claim 1, wherein said acquiring input data comprises determining a normal to each of said plurality of locations.

14. A method as claimed in claim 13, wherein said applying a registration tool comprises applying a registration tool having a flat disc surface at a first end.

15. A method as claimed in claim 14, wherein said applying a registration tool comprises applying a registration tool having a flat disc surface at a second end, said flat disc surface at a second end having different dimensions than said flat disc surface at said first end.

16. A method as claimed in claim 15, wherein said applying a registration tool comprises selecting one of said first end and said second end to apply to said anatomical surface.

17. A method as claimed in claim 1, wherein said acquiring input data comprises acquiring data by rotating said tool to indicate to said position sensing system a location has been selected.

18. A method as claimed in claim 1, wherein said acquiring input data comprises acquiring data by pressing a switch to indicate to said position sensing system a location has been selected.

19. A method as claimed in any one of claims 1 to 18, wherein said anatomical structure is a bone from one of a cadaver and a dummy.

20. A system for displaying an approximate model of a surface of an anatomical structure, the anatomical structure being a bone, the system comprising:
a registration tool having a first end adapted for applying directly in contact against a surface of the bone;
a position sensing system associated to said registration tool for acquiring input data representing a plurality of locations on said surface of the bone acquired at the contact between the registration tool and the bone such that a position and orientation of said registration tool is determined at each of said plurality of locations, the position sensing system associated to at least another surgical tool for tracking said surgical tool;
a storing module for receiving and storing said input data from said position sensing system;
a processing module for processing said input data into an approximate model of said surface of said bone without using an image of the anatomical structure, taken pre-operatively or intra-operatively; and
an output device for displaying said approximate model of said bone with the surgical tool during navigation in surgery, and without any image of the anatomical structure taken pre-operatively or intra-operatively.

21. A system as claimed in claim 20, wherein said processing module processes said input data into a cloud of points forming a mosaic and representing a portion of said anatomical structure.

22. A system as claimed in claim 20, wherein said processing module smoothes over a surface represented by said input data into a smoothed surface of a portion of said anatomical structure.

23. A system as claimed in claim 22, wherein said processing module displays on top of said smoothed surface said locations on said anatomical surface where data was acquired.

24. A system as claimed in claim 20, wherein said processing module reconstructs a three dimensional model, using said input data, into a three dimensional model of a portion of said anatomical structure.

25. A system as claimed in claim 21, comprising a database of known models of varying dimensions, and wherein said processing module attaches a portion of said known models to a portion of said anatomical structure in order to display an entire model.

26. A system as claimed in claim 22, comprising a database of known models of varying dimensions, and wherein said processing module attaches a portion of said known models to a portion of said anatomical structure in order to display an entire model.

27. A system as claimed in claim 24, comprising a database of known models of varying dimensions, and wherein said processing module attaches a portion of said known models to a portion of said anatomical structure in order to display an entire model.

28. A system as claimed in claim 20, said registration tool having a tip adapted for determining a normal associated with each of said plurality of locations on said surface of an anatomical structure, said input data representing a point and its corresponding normal.

29. A system as claimed in claim 28, wherein said tip of said registration tool is a flat disc.

30. A system as claimed in claim 29, wherein said registration tool comprises a second flat disc at an opposite end of said tip, said second flat disc having a smaller radius than said flat disc at said tip.

31. A system as claimed in claim 29, wherein said flat disc has a surface area of 1 $cm^2$.

* * * * *